(12) United States Patent
Wilkins et al.

(10) Patent No.: US 6,812,000 B2
(45) Date of Patent: Nov. 2, 2004

(54) PRODUCT REMOVAL PROCESS FOR USE IN A BIOFERMENTATION SYSTEM

(75) Inventors: Antoinette E. Wilkins, Newark, DE (US); David J. Lowe, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 246 days.

(21) Appl. No.: 10/127,862

(22) Filed: Apr. 22, 2002

(65) Prior Publication Data

US 2003/0166040 A1 Sep. 4, 2003

Related U.S. Application Data (60) Provisional application No. 60/285,555, filed on Apr. 20, 2001.

(51) Int. Cl.[7] .............................. C12P 1/00; C12P 7/18
(52) U.S. Cl. ......................... 435/41; 435/158; 435/175; 435/176; 435/177; 435/178; 435/179; 435/180; 435/181; 435/182; 435/262
(58) Field of Search .................................. 435/174, 175, 435/176, 177, 178, 179, 180, 181, 182, 41, 158, 262

(56) References Cited

U.S. PATENT DOCUMENTS

| | | | |
|---|---|---|---|
| 4,851,573 A | 7/1989 | Kulprathipanja et al. | |
| 5,362,635 A | 11/1994 | Hirose et al. | |
| 5,730,877 A | 3/1998 | Kuisma et al. | |
| 6,114,157 A | 9/2000 | Johnson et al. | |

FOREIGN PATENT DOCUMENTS

| | | |
|---|---|---|
| EP | 0 361 082 A | 4/1990 |
| EP | 0517242 A | 12/1992 |
| WO | WO 97 45185 A | 12/1997 |
| WO | WO 00 33934 A | 6/2000 |
| WO | WO 01 25178 A | 4/2001 |

OTHER PUBLICATIONS

W. Crueger et. al, Biotechnology, pp: 124–174, 1990, a Textbook of Industrial Microbiology, Sinauer Associates: Sutherland, MA.

B. Atkinson et. al., Biochemical Engineering and Biotechnology Handbook, 2nd Ed.; Stockton Press: New York, pp. 243–364, 1991.

Chauhan et. al., Chem Tech, Increasing the productivity of bioconversions processes, vol. 27:28–30, 1997.

Freeman et. al, Biotechnology, In Situ Product Removal as a Tool for Bioprocessing, vol. 11:1007–1012, 1993.

Lye et. al, Trends in Biotechnology, Application of in situ product-removal techniques to biocatalytic processes, vol. 17:395–402, 1999.

LeVan, M.D. in Perry's Chemical Engineers' Handbook, 7th Edition; pp. 16–60; Adsorption and ion Exchange, Perry, R.H., D.W. Green, and J.O. Maloney (EDS); McGraw–Hill: New York; (1997).

Database Scisearch. Acession No. 1999: 177330, Dukler et al., 'Affinity–based in situ product removal coupled with co–immobilization of oily substrate and filamentious fungus.' Journal Molecular Recognition. Feb. 1998, vol. 11 1–6 pp. 231–235, see abstract.

*Primary Examiner*—Herbert J. Lilling (57) ABSTRACT

This invention relates to a bioprocess engineering solution for a product removal process for use in a biofermentation. The invention discloses a process for withdrawing an aliquot of broth from a biofermentation vessel during at least a portion of the biofermentation, removing biocatalyst and water, chromatographically separating biofermentation products from the withdrawn broth using water as an eluent, and returning the remaining components of the broth back to the biofermentation vessel. Process chromatography permits highly selective separation of the target molecule, preventing feedback inhibition of the biofermentation.

13 Claims, 2 Drawing Sheets

PRODUCT REMOVAL PROCESS FOR USE IN A BIOFERMENTATION SYSTEM

This application claims the benefit of U.S. provisional application No. 60/285,555, filed Apr. 20, 2001.

FIELD OF THE INVENTION

This invention relates to a product removal process for use in a biofermentation. More particularly, the instant invention is a process for withdrawing broth from a biofermentation vessel, chromatographically separating biofermentation products from the broth, and returning the remaining components of the broth back to the biofermentation vessel.

BACKGROUND OF THE INVENTION

Biofermentation is an important technology for the biocatalytic conversion of renewable resources. Microbial products produced by means of biofermentation include amino acids, ethanol, and antibiotics. The biofermentative production and commercialization of a few chemicals has been reported (W. Crueger and A. Crueger, *Biotechnology: A Textbook of Industrial Microbiology*, Sinauer Associates: Sunderland, Mass., pp 124–174 (1990); B. Atkinson and F. Mavituna, *Biochemical Engineering and Biotechnology Handbook*, $2^{nd}$ ed.; Stockton Press: New York, pp 243–364 (1991)). Biocatalytic processes, however, frequently suffer from several well-known limitations compared to synthetic processes. These limitations include 1) a relatively small range of products; 2) low yields, titers, and productivities; and 3) difficulty recovering and purifying products from aqueous solutions.

The productivity of a biocatalytic process can be interfered with by accumulating product in several ways. At the biochemical level, feedback inhibition from product accumulation can limit productivity either because of inhibitory effects (which may be reversible) or toxicity effects (which can ultimately kill the microorganism or irreversibly inactivate its biocatalytic components). With regard to cell physiology, accumulating product can deleteriously affect growth rate. Chemical and physical effects (accumulating by-products; pH changes) can also interfere with the productivity of the biocatalyst.

Products of biocatalytic processes may also be lost from the system by 1) degrading from further interaction with the biocatalyst, 2) from environmental conditions, or 3) from uncontrolled removal from the system (i.e., from evaporation).

Although metabolic engineering alone can address some of these limitations, integrating upstream metabolic engineering (i.e., product synthesis) and downstream bioprocess engineering (i.e., product separation and process design) is critical to realize significant value from industrial biofermentations.

In situ product removal (ISPR) methodologies are a family of techniques in which a target molecule in the biofermentation (either a biofermentation product or other specific byproducts) is removed as it is synthesized during at least a portion of the biofermentation process (reviewed in Chauhan et al., *Chem Tech* 27: 26–30 (1997); and Freeman et al., *Biotechnology* 11: 1007–1012 (1993)). Since a variety of separation principles can be used for ISPR, including those based on different volatility, solubility, size, density, charge, or specific elements (or combinations of these methods), ISPR techniques have wide applicability. A number of ISPR techniques have been integrated into biocatalytic processes based upon Amberlite XAD resins, continuous precipitation, reactive solvent extraction followed by simultaneous extraction and back extraction, and an extractive hollow-fiber membrane reactor (Lye et al., *Trends in Biotechnology* 17:395–402 (1999)).

A key challenge to successful use of ISPR in biofermentations is how to apply separation technology to large-scale industrial processes in a cost- and time-effective manner that increases productivity. One bioengineering factor that significantly affects productivity of a biofermentation recovery and purification system is the mode of process operation. Those skilled in the art know that it is generally more cost- and time-effective to rely on a continuous separation method versus a purely batch process.

U.S. Pat. No. 6,114,157 illustrates the challenges of using ISPR techniques cost- and time-effectively. The patent describes an ISPR method for increasing total production of 4-hydroxybenzoic acid (PHB) by biofermentation. Genetically engineered *E. coli* cells produce PHB during the biofermentation. For at least a portion of the biofermentation, the biofermentation broth passes through a bed of anion exchange beads in an upwards direction. The biofermentation medium depleted of PHB then returns to the biofermentor. This process cycled the entire culture volume through the beads every ten minutes, with no need for media replacement. When the anion exchange beads became saturated, the biofermentation was stopped, and PHB was extracted from the resin with acidic ethanol or sodium chloride in a water/ethanol mixture.

Although U.S. Pat. No. 6,114,157 does disclose ISPR separation of a biofermentation product, with media recycling back to the biofermentor, the effectiveness of the method is limited by its reliance on expanded bed adsorption. Expanded bed adsorption is not a continuous process, but instead requires a strategy of "load and elute" which means increased process time for isolating product with multi-step processes. The method is therefore not cost- or time-efficient for large-scale commercial applications. For example, adsorbent beads require a water rinse before elution, and may also require reconditioning with phosphate buffer before each reuse. U.S. Pat. No. 6,114,157 discloses an expanded bed adsorber that is approximately equivalent to half the size of the biofermentor. In industrial practice, this would add significantly to the commercial investment. Further, non-efficient use of resin and eluent would significantly increase the cost for large-scale commercial applications. Specifically, the volume of ethanol to elute product is large, relative to the amount of product recovered, and the ethanol may gradually evaporate during regeneration of the expanded beds. The eluent also requires one molar equivalent of trifluoroacetic acid, a costly additive. Additionally, biofermentation with microorganisms having high respiration rates could not use expanded bed adsorption for product separation, since dissolved oxygen content in the expanded bed would be low for extended periods. This would be severely detrimental to microorganism viability. In addition to limitations inherent in the use of expanded bed adsorption, U.S. Pat. No. 6,114,157 does not describe a process for separating neutrally charged products, for which ion exchange methods are not generally effective.

One ISPR separation technology that is operative and cost- and time-efficient at the process or production scale (in contrast to the analytical or preparative scale) is simulated moving bed (SMB) chromatography. This technique is a continuous chromatographic process, which relies on counter-current chromatography or simulated counter-current chromatography to achieve a separation (LeVan, M.

D. In *Perry's Chemical Engineers' Handbook, 7th Edition*; p.16–60; Perry, R. H., D. W. Green, and J. O. Maloney (Eds.); McGraw-Hill: New York; (1997)). This is widely recognized as a solvent-saving, efficient technology (U.S. Pat. No. 4,851,573, column 11). The operating principles for SMB chromatography are described in U.S. Pat. No. 2,985,589. Use of SMB chromatography is now an established technique for production-scale applications. Other process chromatography methods include, but are not limited to, cross-flow chromatography and radial chromatography. However, as currently practiced, process chromatography methods are unable to selectively separate biofermentation products and recycle the other media components to the biofermentor. This occurs because a portion of the eluent required to drive chromatographic separation would accumulate in the biofermentor, reducing its capacity. Although the duration of the biofermentation can be lengthened to increase productivity, continual media replacement increases costs for large-scale manufacturing. This is especially true when the biofermentation media contains costly cofactors and other required components for the biocatalysts' growth.

Thus, the problem to be solved is the lack of a bioprocess engineering method to selectively remove interfering target molecules produced during the biofermentation reaction without adding fresh media or accumulating eluent in the biofermentor. Ideally, the bioprocess engineering method would: 1) remove the target molecule causing toxicity or feedback inhibition of the bioprocess, 2) alleviate replacement of media withdrawn from the biofermentor for ISPR, and 3) prevent eluent accumulation in the biofermentor. Such a technique would greatly improve bioprocess performance, increasing the total production rate of the biocatalyst. As a result, higher capital productivity and potentially higher reaction yields would be achieved.

SUMMARY OF THE INVENTION

The invention provided herein is a product removal process for use in a biofermentation system comprising: a) removing (during at least a portion of the biofermentation) at least a majority of biocatalyst from a portion of biofermentation solution containing a target molecule; b) removing a portion of water from the biocatalyst-free solution produced in step a); c) optionally before or after step b) removing components other than the target molecule from the biocatalyst-free solution; d) feeding through a chromatographic medium 1) the biocatalyst-free solution produced by any of the steps of b) or c), and 2) an eluent; e) recovering the target molecule from a first fraction of the biocatalyst-free solution discharged from the chromatographic medium; f) optionally removing non-aqueous eluent from a second fraction of the biocatalyst-free and target molecule-free solution discharged from the chromatographic medium; g) optionally adding water removed from the biocatalyst-free solution in step b) to the biocatalyst-free and target molecule-free solution after steps e) or f) in an amount suitable for return to the biofermentation; and h) returning the biocatalyst-free and target molecule-free solution from any of the steps of d), e), f), or g) to the biofermentation.

An alternate embodiment of the invention removes a product when the target molecule has a higher vapor pressure than water at the temperature used in the water removal step. This alternate embodiment prevents preferential evaporation of the target molecule before passage into the process chromatograph.

The eluent used in the process may be water removed from the biofermentation or water mixed with a non-aqueous eluent. The non-aqueous eluent is a short chain alcohol or acetone. The water removed in the process from the biocatalyst-free solution is preferably from 50–80%. The invention selectively removes any target molecule from the biofermentation. One embodiment of the invention selectively removes 1,3-propanediol.

Additionally, an embodiment of the invention is a system for in situ target molecule removal from a biofermentation as described herein. The system includes a) a biocatalyst separation means to remove at least a majority of biocatalyst from a portion of the biofermentation solution containing a target molecule; b) a water removal means for removing a portion of water from the biocatalyst-free solution produced by the biocatalyst separation means of a) in step a); c) optionally before or after step b) a removal means to remove components other than the target molecule or water from the biocatalyst-free solution produced by the water removal means of b); d) a process chromatographic means through which the concentrated biocatalyst-free solution produced by the water removal means of b) or by the removal means of c) and an eluent are passed; e) a target molecule recovery means to recover the majority of the target molecule from a first fraction of the discharge from the chromatographic means of d); f) optionally a non-aqueous eluent removal means to remove non-aqueous eluent from a second fraction discharged from the chromatographic means of d); g) a water adding means to add water generated by b) to the biocatalyst-free and target molecule-free solution produced from e) or f) in an amount suitable for return to the biofermentation; and h) a media recycle means to return the biocatalyst-free and target molecule-free solution from d), e), f), or g) to the biofermentation. The system can be modified to remove product when the target molecule has a higher vapor pressure than water at the temperature used in the water removal step.

BRIEF DESCRIPTION OF THE DRAWINGS, BIOLOGICAL DEPOSIT, AND SEQUENCE LISTING

Applicants have made the following biological deposit under the terms of the Budapest Treaty:

| Depositor Identification Reference | Int'l. Depository Designation | Date of Deposit |
|---|---|---|
| *Escherichia coli* RJ8n | ATCC PTA-4216 | 9 Apr. 2002 |

As used herein, "ATCC" refers to the American Type Culture Collection International Depository located 10801 University Blvd., Manassas, Va. 20110-1109, U.S.A. The "ATCC No." is the accession number to cultures on deposit with the ATCC.

The listed deposit will be maintained in the indicated international depository for at least thirty (30) years and will be made available to the public upon grant of a patent disclosing it. The availability of a deposit does not constitute a license to practice the subject invention in derogation of patent rights granted by government action.

Applicants have provided one sequence in conformity with Rules for the Standard Representation of Nucleotide and Amino Acid Sequences in Patent Applications (Annexes I and II to the Decision of the President of the EPO, published in Supplement No. 2 to OJ EPO, 12/1992), with 37 C.F.R. 1.821–1.825 and Appendices A and B (Requirements for Application Disclosures Containing Nucleotides and/or Amino Acid Sequences) with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The Sequence Descriptions contain the one letter code for nucleotide sequence characters and the three letter codes for amino acids as defined in conformity with the IUPAC-IYUB standards described in *Nucleic Acids Research* 13:3021–3030 (1985) and in the *Biochemical Journal* 219 (No. 2):345–373 (1984) which are herein incorporated by reference.

SEQ ID NO.:1 is the nucleotide sequence for the plasmid pSYCO103.

DETAILED DESCRIPTION OF THE INVENTION

Applicants have solved the stated problem. The present invention provides a bioprocess engineering solution allowing selective process chromatographic removal of a target molecule during a biofermentation using in situ product removal and recycle of the remaining biocatalyst-free broth back to the biofermentation vessel. By using the system's broth as the source of at least a portion of the chromatographic eluent and recycling the medium, the present invention simplifies the overall bioprocess, reduces the need to replace the medium, reduces the effects of feedback inhibition or toxicity on the biocatalyst, and/or prevents eluent accumulation in the biofermentation vessel.

The invention lowers costs for isolating target molecules from a biofermentation broth for industrial or commercial use and improves the productivity of the biofermentation by removing interfering target molecules. The invention makes use of relatively simple equipment and allows relatively easy maintenance. The size of the units which can profit from this invention can vary from those of laboratory scale to those of commercial scale and can range in flow rates from as little as a few milliliters per hour to many thousands of gallons per hour.

Applicants' invention is useful for improving the productivity of any biofermentation process using a biocatalyst producing a product interfering with the biofermentation due to feedback inhibition or toxicity, or lost because of product degradation, environmental conditions, or uncontrolled removal from the system, or where simplifying product recovery processes is desirable.

In the application, unless specifically stated otherwise, the following abbreviations and definitions apply:

"Product removal process" refers to a process whereby a portion of the biofermentation system is withdrawn from the biofermentation vessel during at a least portion of the biofermentation for selective product removal. The product, or target molecule, is then selectively removed from the broth.

"In situ product removal" is abbreviated ISPR. In the instant invention, ISPR is performed externally (i.e., outside the biofermentation vessel) in a separate process loop through which a fraction of the medium is circulated specifically for product removal. Alternatively, ISPR could be performed directly within the biofermentation vessel.

"Biofermentation system" or "biofermentation" refers to a system that catalyzes a reaction between substrate(s) to product(s) through use of a biocatalyst. The "biocatalyst" initiates or modifies the rate of a chemical reaction between substrate(s) and product(s). The biocatalyst can be a whole microorganism, an isolated enzyme, or any combination thereof. For purposes of this application, "microorganism" also encompasses cells from insects, animals, or plants.

"Broth" or "medium" refer to a liquid solution containing nutrients for culturing microorganisms. The broth may additionally contain the biocatalyst, target molecules produced by the biocatalyst, metabolic intermediates, and other media components such as salts, vitamins, amino acids, cofactors, and antibiotics.

"Target molecule" refers to any biocatalytically-produced product that is selectively removed from the biofermentation using the process herein described. This may be a compound that is naturally produced by the biocatalyst or non-native genes may be genetically engineered into a microorganism for their functional expression in the biofermentation. "Target molecule" in this context also refers to any by-product of the biofermentation that would be desirable to selectively remove from the biofermentation system to eliminate feedback inhibition and/or to maximize biocatalyst activity.

"Biocatalyst-free solution" refers to broth removed from the biofermentation from which at least the majority of the biocatalyst material has been removed. The biocatalyst-free solution may be a permeate (produced following passage of the biofermentation broth through a membrane) or a supernatant. Components in the biocatalyst-free solution may include target molecules produced by the biocatalyst, metabolic intermediates, and other media components such as salts, vitamins, amino acids, cofactors, and antibiotics.

"Biocatalyst-free and target molecule-free solution" refers to broth removed from the biofermentation from which at least the majority of both the biocatalyst and the target molecule have been removed. Components optionally remaining in the biocatalyst-free and target molecule-free solution could comprise a significantly reduced concentration of target molecules, metabolic intermediates, and other media components such as salts, vitamins, amino acids, cofactors, and antibiotics.

"Chromatographic medium" refers to any material used as part of a chromatography system to separate components in the input feed streams which consist of an eluent and a biocatalyst-free solution.

"Volumetric productivity" refers to the mass of target molecule produced in a biofermentor in a given volume per time, with units of grams/(liter hour) (abbreviated g/(L hr)). This measure is determined by the specific activity of the biocatalyst and the concentration of the biocatalyst. It is calculated from the titer, run time, and the working volume of the biofermentor.

"Titer" refers to the target molecule concentration with units of grams/liter (abbreviated g/L).

Although the present invention is described below in terms of a process chromatograph to effectively separate target molecules from the biocatalyst-free solution, a variety of chromatographic separation methodologies are operative in the invention at the process or production scale (in contrast to the analytical or preparative scale). These alternative embodiments of the invention would include, but are not limited to, simulated moving bed (SMB) chromatography, cross-flow chromatography, or radial chromatography to selectively separate the target molecule from the biofermentation broth.

Figure 1:
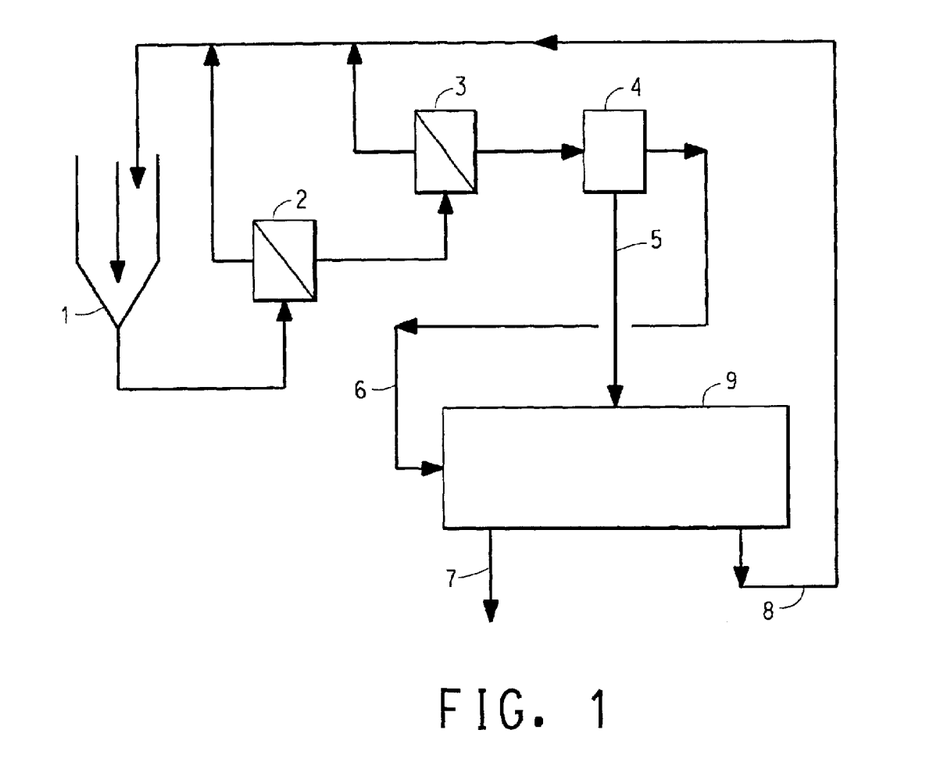
FIG. 1 is a process flow diagram illustrating the preferred arrangement of elements enabling target molecule recovery and recycle of biocatalyst-free and target molecule-free solution to the biofermentation vessel.

In a preferred embodiment and with reference to FIG. 1, a biofermentation vessel (1) is set up with a broth recirculation loop, which includes a cross-flow filtration unit (2), a water removal unit (4), and a process chromatograph (9). The setup allows removal of broth from the biofermentation vessel (1) and its passage through the cross-flow filtration unit (2). Biocatalyst and a portion of the broth are returned to the biofermentation vessel (1), while the biocatalyst-free solution produced via passage through the cross-flow filtration unit (2) is concentrated in the water removal unit (4). Concentrated biocatalyst-free solution (5) then passes through the process chromatograph (9) with water eluent (6) generated in the water removal unit (4). This chromatographic separation isolates the majority of the target molecule (7) from the remainder of the concentrated biocatalyst-free solution. The biocatalyst-free and target molecule-free solution (8) is recycled, by return to the biofermentation vessel (1).

Figure 2:
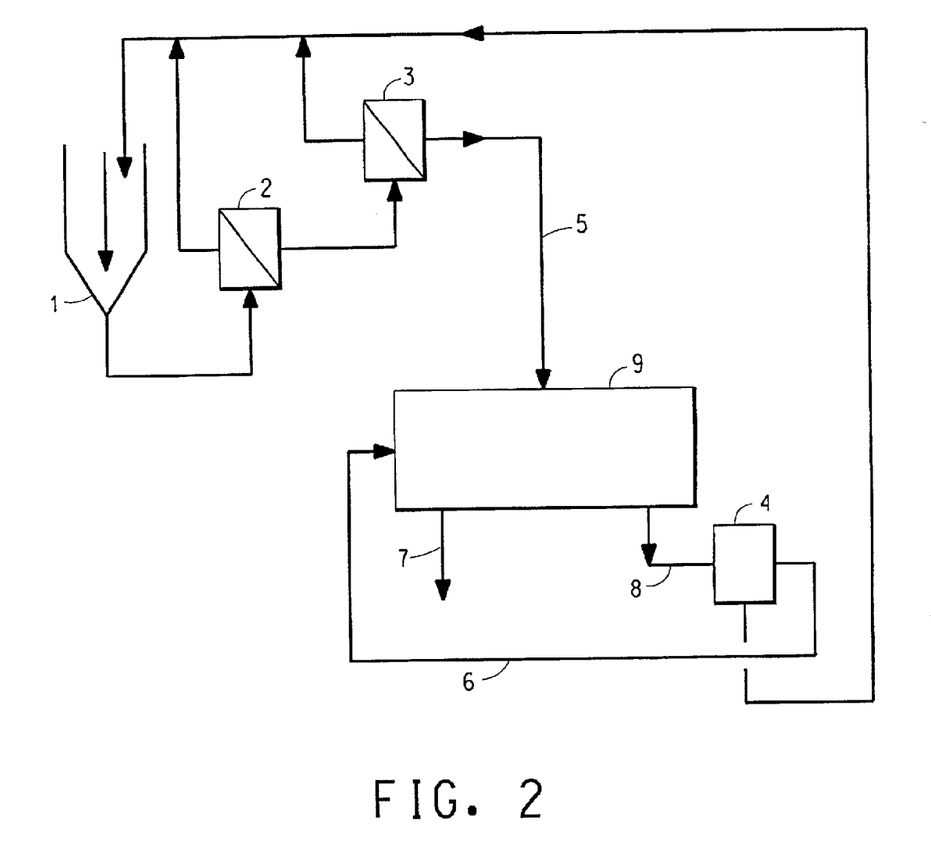
FIG. 2 is a process flow diagram illustrating the invention in an alternative embodiment to remove a product when the target molecule has a higher vapor pressure than water at the temperature used in the water removal step.

In an alternate embodiment of the invention disclosed above and with reference to FIG. 2, the invention is modified to remove product when the target molecule has a higher vapor pressure than water at the temperature used in the water removal step (4). A biofermentation vessel (1) is set up with a broth recirculation loop, which includes a cross-flow filtration unit (2), a water removal unit (4), and a process chromatograph (9). The setup allows removal of broth from the biofermentation vessel (1) and its passage through the cross-flow filtration unit (2). Biocatalyst and a portion of the broth are returned to the biofermentation vessel (1) while the biocatalyst-free solution produced via passage through the cross-flow filtration unit (2) is immediately fed into the process chromatograph (9) with water eluent (6) generated in the water removal unit (4). Chromatographic separation isolates the majority of the target molecule (7) from the remainder of the biocatalyst-free solution. The biocatalyst-free and target molecule-free solution (8) is then concentrated in the water removal unit (4), before the solution returns to the biofermentation vessel (1).

The skilled artisan is well aware that where the target molecule had a higher vapor pressure than water at the temperature used in the water removal step, this process modification would be necessary to prevent preferential evaporation of the target molecule before it passed into the process chromatograph. Likewise, this alternative embodiment would also be necessary if reverse osmosis was used as the method for water removal and the target molecule produced by the biofermentation has a higher vapor pressure than water at the temperature used in the water removal step. This would again permit target molecule removal before the water removal step (4). Variations to the basic invention can be envisioned. Many of these embodiments are discussed below.

The rate at which biocatalyst-free solution is removed from the biofermentation vessel (1) and moves through the process flow of the invention before recycling to the biofermentation vessel (1) is critical to maintaining the target molecule concentration in the biofermentation vessel (1) below the feedback inhibitory or toxic threshold of the biocatalyst. Methods to determine the parameters to maintain this circulation rate are well known to the skilled artisan.

Particular aspects of the invention are discussed in greater detail below.

Separation of Biofermentation Broth:

A separation of solid (i.e., biocatalyst) from liquid initially occurs when broth is removed from the biofermentation vessel (1). This separation yields a biocatalyst-free solution while allowing return of the biocatalyst material and a portion of the supernatant to the biofermentation vessel (1). Various solid-liquid separation methods are available and include, but are not limited to, cross-flow filtration, centrifugation, and dead-end filtration. It would also be possible to use conventional filtration while placing a biocompatible filter aid within the biofermentation vessel (1).

A cross-flow filtration unit (2) separates an influent stream into two effluent streams. The biocatalyst-free solution (or permeate) is the portion of the effluent fluid that passes through a membrane. The second effluent stream contains the cellular material of the biocatalyst and the supernatant that is rejected by the membrane. This second effluent stream is immediately returned to the biofermentation vessel (1).

The particular membrane used for cross-flow filtration depends on the size of the particles to be removed from the influent stream. Typical sizes would be those generally used for microfiltration and ultrafiltration, with pore sizes about 0.2 micron and smaller. Preferred membranes include cellulosic, polyamide, polysulfone, and polyvinylidene fluoride.

In addition to membrane selection, the combined effects of temperature, pressure, and contaminant fouling must be carefully considered to ensure successful operation of a cross-flow filtration unit. The chemical compatibility and membrane stability at a given process stream pH are also factors. These conditions may be optimized readily by one skilled in the art.

Filtration of Biocatalyst-Free Solution:

An optional additional filtration (3) can be used in the product removal process by a second stage cross-flow filtration unit with more selective membranes or smaller pore sizes. This optional filtration would remove other components from the biocatalyst-free solution, such as proteins, protein fragments, divalent salts, monovalent ions, or organics. Using a second stage filtration unit potentially increases the life of the chromatographic absorbent.

Temperature:

It is well known to the skilled chromatographic artisan that separation may be affected by the temperature of the input feed. A heat exchanger could optionally be added to the water removal unit. This heat exchanger would facilitate both chromatographic separation and evaporation, such that it occurred at a consistent and predictable rate.

Water Removal:

Distillation, reverse osmosis, vapor recompression, or simple evaporation may be used to remove water (4) from the biocatalyst-free solution. In a preferred embodiment, the water removal step would remove approximately 50 to 80% of water from the biocatalyst-free solution to yield a biocatalyst-free solution significantly more concentrated than that produced initially after removal from the biofermentation vessel (1). This concentrated biocatalyst-free solution would contain target molecules. It would also contain other media components (e.g., salts, vitamins, amino acids, cofactors, antibiotics, and metabolic intermediates) which ultimately are returned to the biofermentation vessel (1). Trace volatiles, formed as a byproduct of the biofermentation, may be removed from the biocatalyst-free solution if their boiling point is near or below that of water.

Target Molecule Separation via Passage through a Chromatographic Medium:

Virtually any type of target molecule could be chromatographically separated from a biofermentation solution by use of this invention. This invention is adaptable to separating neutral and charged target molecules, target molecules with molecular weights of small molecules to large secreted proteins, and of chiral molecules. Highly selective separation of the target molecule occurs via passage of the biocatalyst-free solution through the process chromatograph (9). A preferred target molecule is bio-processed 1,3-propanediol (U.S. Pat. No. 5,686,276).

In all cases, separating the target molecule from the biocatalyst-free solution typically relies on the level of molecular interaction with the chromatographic medium or adsorbent. Adsorbents include, but are not limited to, activated carbon, zeolites, polymeric neutral resins, chitosan beads, ion-exchange resins, and immobilized complexation materials. Selection of a particular adsorbent will depend on a variety of factors, well known to those skilled in the art. Such factors include, but are not limited to, charge of the target molecule, size of the target molecule, rates of adsorption and desorption, chemical and physical interactions with the surface, stability of the absorbent (e.g., zeolites exchanging ions with salts in the liquid), and biotoxicity of the adsorbent. Additional considerations include the particular application and target molecule, media stability, the chromatographic method, and the scale of the process and equipment.

In a preferred embodiment in which the target molecule is not more volatile than water, a first fraction (containing the target molecule and chromatographic eluent) is discharged from the chromatographic medium. Target molecule separation occurs based on affinity of the target molecule for the chromatographic medium. Reversibility of the target molecule binding/complexation is achieved by virtue of the differential migration of the target molecule compared to other solutes in the biocatalyst-free solution. This permits facile elution from the adsorbent. Elution conditions will include the same range of temperatures and pressures as used for adsorption conditions. The target molecule-eluent mixture recovered from the chromatograph is then refined by methods well known in the art (for example, distillation).

Alternatively, separation may result without target molecule affinity for the chromatographic medium. For example, some target molecules, having no interaction with the adsorbent, could be discharged first from the chromatograph while other components in the biocatalyst-free solution would have longer retention times because of their affinity for the adsorbent. The mixture of eluent and diluted biocatalyst-free and target molecule-free solution is discharged as a second fraction from the chromatograph.

The Chromatographic Eluent and "Media Recycle":

In a preferred embodiment of the present invention, the eluent fed into the chromatograph is water generated by the water removal unit (4). Because the water removal unit reduces the water content of the biocatalyst-free solution by approximately 50–80%, the biocatalyst-free solution fed into the chromatograph is significantly more concentrated in solutes than the biocatalyst-free solution produced initially upon removal from the biofermentation vessel (1). When water eluent is later added to this concentrated solution, the resulting overall water content is not greater than that of the biocatalyst-free solution produced initially upon removal from the biofermentation vessel (1). When water eluent is later added to this concentrated solution, the resulting overall water content is not greater than that of the biocatalyst-free solution produced initially upon removal from the biofermentation vessel (1).

Many process advantages follow from use of water collected from the water removal unit (4) as the chromatographic eluent. This "media recycling" technique directly reduces costs that would otherwise be incurred replacing the biocatalyst-free solution removed from the biofermentation vessel (1) for ISPR with additional new media. This permits remaining components of the broth, such as salts, vitamins, amino acids, cofactors, antibiotics, and metabolic intermediates (minus the purified target molecule) to be returned to the biofermentation vessel (1).

Further, the media recycling process does not increase overall volume in the biofermentation vessel (1) since the biocatalyst-free solution is first concentrated and then rehydrated. This eliminates concerns of eluent, accumulating in the biofermentation vessel (1), substantially changing the fermentative broth composition and/or reducing the capacity of the biofermentation vessel (1).

The media recycling process could also be used to remove water from the biofermentation vessel (1). This could be especially advantageous should the biofermentation be run in fed-batch mode, with incremental addition of a substrate dissolved in water. Overall water balance in the biofermentation vessel (1) could thereby be maintained.

Finally, re-use of water collected from the water removal unit as the chromatographic eluent reduces the number of operational units in the system. Specifically, water re-use eliminates the need for a separate source of sterilized water suitable to enter the biofermentation. Operating costs are further reduced, since water re-use avoids constructing industrial water treatment and purification facilities that would be required if the eluent was discharged into the environment.

In an alternate embodiment of the invention, a non-aqueous eluent (such as short chain alcohols, ethanol, or acetone) could be used (alone or in combination with water) for chromatography. The target molecule-eluent mixture recovered from the chromatograph discharge is then refined by methods well known in the art (for example, distillation). The second fraction discharged from the process chromatograph (9) containing the mixture of eluent and diluted biocatalyst-free and target molecule-free solution could be passed through various separating devices (such as flash evaporation or a packed bed absorber) to remove non-aqueous eluent. The non-aqueous eluent could be recycled to the chromatographic medium, while the concentrated biocatalyst-free and target molecule-free solution could be optionally rehydrated with water and then returned to the biofermentation vessel (1) as "media recycle".

Biofermentations

The present invention is adaptable to a variety of biofermentation methodologies, especially those suitable for large-scale industrial processes. The invention may be practiced using batch, fed-batch, or continuous processes, but is preferably practiced in fed-batch mode.

It is possible to calculate and compare the differences in process economics for a batch versus a continuous process. Using a standard set of conditions, a continuous system can be approximately 70 times more efficient in terms of productivity/adsorbent and eluent consumption can be reduced by a factor of 8 as compared to a batch process (Table 1, extracted from Rossiter et al., "Continuous Process Separation: Chiral & Chromatographic with CSEP™ and ISEP™; Advanced Separation Technologies. Prep 97 Meeting, Washington, D.C.; p 12 (1997)).

Batch and Fed-Batch Biofermentations

Classical batch biofermentation is a closed system where the composition of the broth is set at the beginning of the biofermentation and not subjected to artificial alterations during the biofermentation. Thus, at the beginning of the biofermentation the broth is inoculated with the desired microorganism or organisms and biofermentation proceeds without further addition to the system. Typically, however, "batch" biofermentation is batch with respect to the addition of carbon source and attempts are often made at controlling factors such as pH and oxygen concentration. In batch systems the metabolite and biomass compositions of the system change constantly up to the time the biofermentation is stopped. Within batch cultures cells moderate through a static lag phase to a high-growth log phase and finally to a stationary phase where growth rate is diminished or halted. If untreated, cells in the stationary phase will eventually die. Cells in log phase generally are responsible for the bulk of production of end product or intermediate, when the product is growth associated.

A variation on the standard batch system is the fed-batch system. The present process preferably uses a fed-batch method of biofermentation. Fed-batch biofermentation processes comprise a typical batch system with the exception that the substrate is added in increments as the biofermentation progresses. Fed-batch systems are useful when catabolite repression is apt to inhibit the metabolism of the cells and where it is desirable to have limited amounts of substrate in the media. Measuring actual substrate concentration in fed-batch systems is difficult and is therefore estimated on the basis of the changes of measurable factors such as pH, dissolved oxygen, and the partial pressure of waste gases such as $CO_2$. Batch and fed-batch biofermentation are common and well known in the art (Brock, T. D.; *Biotechnology: A Textbook of Industrial Microbiology*, 2nd ed.; Sinauer Associates: Sunderland, Mass. (1989); or Deshpande, *Appl. Biochem. Biotechnol.* 36:227 (1992)).

Continuous Biofermentation

In a continuous biofermentation system, a defined biofermentation solution is added continuously to a bioreactor and an equal amount of biofermentation solution is removed simultaneously for processing. Continuous biofermentation generally maintains the cultures at a constant high density where cells are primarily in log phase growth. The methodology allows modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to operate under steady state growth conditions and balance cell loss due to biofermentation solution being drawn off against cell growth rate in the biofermentation. Methods of modulating nutrients and growth factors for continuous biofermentation processes as well as techniques for maximizing the rate of product formation, are well known in the art of industrial microbiology (Brock, supra).

The Biocatalyst

The biocatalyst may be whole microorganisms or in the form of isolated enzyme catalysts. Whole microbial cells can be used as biocatalyst without any pretreatment such as permeabilization. Alternatively, the whole cells may be permeabilized by methods familiar to those skilled in the art (e.g., treatment with toluene, detergents, or freeze-thawing) to improve the rate of diffusion of materials into and out of the cells.

An *E. coli* strain, RJ8n transformed with the plasmid pSYCO103, was used as the biocatalyst for the bioproduction of 1,3-propanediol.

RJ8n comprises (a) a set of three endogenous genes, each gene having a mutation inactivating the gene, the set consisting of (i) glpk, a gene encoding glycerol kinase, (ii) gldA, a gene encoding glycerol dehydrogenase, and (iii) tpiA, a gene encoding triosephosphate isomerase, and (b) at least one endogenous gene encoding a non-specific catalytic activity sufficient to convert 3-hydroxypropionaldehyde to 1,3-propanediol. The plasmid pSYCO103 (SEQ ID NO.:1) comprises a set of seven exogenous genes: (i) three genes encoding a glycerol dehydratase (E.C. 4.2.1.30), (ii) two genes encoding a dehydratase reactivation factor (WO 01/12833 A3) (iii) one gene encoding a glycerol-3-phosphate dehydrogenase (EC 1.1.1.8), and (iv) one gene encoding a glycerol-3-phosphatase (EC 3.1.3.21).

In addition to the particular *E. coli* strain referred to above, microorganisms useful in the present invention may include, but are not limited to, bacteria (such as the enteric bacteria Escherichia and Salmonella, for example, as well as Bacillus, Acinetobacter, Streptomyces, Methylobacter, Rhodococcus, and Pseudomonas); Cyanobacteria (such as Rhodobacter and Synechocystis); yeasts (such as Saccharomyces, Zygosaccharomyces, Kluyveromyces, Candida, Hansenula, Debaryomyces, Mucor, Pichia, and Torulopsis); filamentous fungi (such as Aspergillus and Arthrobotrys); and algae. The skilled artisan will also recognize that the present invention could also be applicable to cultures of cells from insects, plants, and animals.

The enzyme biocatalyst can be immobilized in a polymer matrix (e.g., alginate, carrageenan, polyvinyl alcohol, or polyacrylamide gel (PAG) particles) or on a soluble or insoluble support (e.g., celite) to facilitate recovery and reuse of the biocatalyst. Methods for immobilizing biocatalysts in a polymer matrix or on a soluble or insoluble support have been widely reported and are well known to those skilled in the art.

Culture Conditions

Materials and methods suitable for maintenance and growth of microbial cultures are well known to those in the art of microbiology or biofermentation science art (Bailey, J. E. and Ollis, D. F., *Biochemical Engineering Fundamentals*, $2^{nd}$ Edition; McGraw-Hill: NY (1986)). Consideration must be given to appropriate media, pH, temperature, and requirements for aerobic, microaerobic, or anaerobic conditions, depending on the specific requirements of the microorganism for the desired functional gene expression.

Media and Carbon Substrates:

Large-scale microbial growth and functional gene expression may use a wide range of simple or complex carbohydrates, organic acids and alcohols, and saturated hydrocarbons. Biofermentation media in the present invention must contain suitable carbon substrates, chosen in light of the needs of the biocatalyst. Suitable substrates may include, but are not limited to, monosaccharides (such as glucose and fructose), disaccharides (such as lactose or sucrose), oligosaccharides and polysaccharides (such as starch or cellulose or mixtures thereof), or unpurified mixtures from renewable feedstocks (such as cheese whey permeate, cornsteep liquor, sugar beet molasses, and barley malt). The carbon substrate may also be one-carbon substrates (such as carbon dioxide, methanol, or methane).

In addition to an appropriate carbon source, biofermentation media must contain suitable minerals, salts, cofactors, buffers, and other components, known to those skilled in the art (Bailey, J. E. and Ollis, D. F., *Biochemical Engineering Fundamentals*, $2^{nd}$ ed; pp 383–384 and 620–622; McGraw-Hill: New York (1986)). These supplements must be suitable for the growth of the biocatalyst and promote the enzymatic pathway necessary to produce the biofermentation product. In the case of the present invention, the carbon source and the other components described above are separated from the target molecule and returned to the biofermentation vessel.

Finally, functional genes that express an industrially useful product may be regulated, repressed, or derepressed by specific growth conditions (for example, the form and amount of nitrogen, phosphorous, sulfur, oxygen, carbon or any trace micronutrient including small inorganic ions). The regulation of functional genes may be achieved by the presence or absence of specific regulatory molecules (such as gratuitous inducers) that are added to the culture and are not typically considered nutrient or energy sources. Growth rate may also be an important regulatory factor in gene expression.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

The meaning of abbreviations is as follows: "h" means hour(s), "min" means minute(s), "sec" means second(s), "d" means day(s), "mL" means milliliter(s), "L" means liter(s), "g" means gram(s), "kg" means kilogram(s), "atm" means atmosphere(s).

General Methods:

Materials and methods suitable for the maintenance and growth of bacterial cultures are well known in the art. Techniques suitable for use in the following examples may be found as set out in *Manual of Methods for General Bacteriology*; Phillipp Gerhardt, R. G. E. Murray, Ralph N. Costilow, Eugene W. Nester, Willis A. Wood, Noel R. Krieg and G. Briggs Phillips, Eds., American Society for Microbiology: Washington, D.C. (1994) or in *Biotechnology: A Textbook of Industrial Microbiology*; Brock, T. D., $2^{nd}$ ed.; Sinauer Associates: Sunderland, Mass. (1989).

Example 2 demonstrates a steady state process computer simulation using Aspenplus™ software Release 10.1 from Aspen Technology, Inc., Cambridge, Mass. Aspenplus™ does not have a specific unit operation for process chromatography. A simulated moving bed (SMB) process chromatograph was modeled using the EXTRACT block, which is normally used for countercurrent liquid—liquid extraction. Dodecane was used as one of the liquid phases to simulate the solid phase. The liquid—liquid equilibria constants were set as shown in Table 2 based on results of batch chromatography experiments, with one exception. Specifically, the liquid-liquid-equilibria constants for water and dodecane were set at arbitrary high and low values, respectively.

Example 1

Comparative Example (Without Media Recycle)

This experiment was carried out for comparison purposes to illustrate volumetric productivity in the absence of media recycle.

A fed-batch biofermentation was run using glucose as the substrate to produce 1,3-propanediol. An *E. coli* strain, RJ8n transformed with the plasmid pSYCO103, was used as the biocatalyst in the bioprocess.

*E. coli* RJ8n strain (ATCC PTA-4216) comprises (a) a set of three endogenous genes, each gene having a mutation inactivating the gene, the set consisting of (i) glpK, a gene encoding glycerol kinase, (ii) gldA, a gene encoding glycerol dehydrogenase, and (iii) tpiA, a gene encoding triose-phosphate isomerase, and (b) at least one endogenous gene encoding a non-specific catalytic activity sufficient to convert 3-hydroxypropionaldehyde to 1,3-propanediol. The plasmid pSYCO103 (SEQ ID NO.:1) comprises a set of seven exogenous genes: (i) three genes encoding a glycerol dehydratase (E.C. 4.2.1.30), (ii) two genes encoding a dehydratase reactivation factor (WO 01/12833 A3) (iii) one gene encoding a glycerol-3-phosphate dehydrogenase (EC 1.1.1.8), and (iv) one gene encoding a glycerol-3-phosphatase (EC 3.1.3.21).

A 10 liter working volume biofermentor was prepared using components and methods known in the art. Media was prepared using components (e.g., water, salts, yeast extract) and methods known in the art. The inoculum was prepared in shake flasks using methods known in the art.

The fermentation was run for 68 h after inoculation. Glucose control was accomplished by analyzing a sample every two h and adjusting the glucose solution feed rate based on an aim point of 10 g glucose/L.

In avoid overfilling the fermentor, 3.44 L of broth were drained from the biofermentor 40 h after inoculation.

The volumetric productivity of the biofermentor was calculated by measuring the 1,3-propanediol titer in the fermentor by liquid chromatography and calculating the mass of 1,3-propanediol that would have been produce if that titer had been produced in the liquid in the biofermentor plus the liquid volume that had been drained.

1,3-Propanediol may be identified directly by submitting the media to high performance liquid chromatography (HPLC) analysis. Preferred in the present invention is a method where fermentation media is analyzed by ion moderated partition chromatography (IMP) with 0.01N sulfuric acid as mobile phase and in an isocratic fashion. In all of the examples, the concentration of 3 G was measured by HPLC.

A Waters 715 autosampler, Waters temperature control module (set point 50° C.), Waters 410 refractive index detector, and Waters 486 UV detector (wavelength=210 nm) was equipped with a Shodex HPLC column (SH1011 sugar column, 300 mm×8 mm) for 1,3-propanediol quantitation. Mobile phase was 0.005 molar sulfuric acid at 0.5 mL/min isocratic flow. Pivalic acid was used as an internal standard. Under these conditions, 1,3-propanediol elutes at 25.9 min.

The maximum volumetric productivity was 15.85 kg/m³/yr, which was observed at 41.85 h after inoculation. The volumetric productivity was calculated by dividing the amount of 1,3-propanediol produced (from the titer multiplied by the total volume of broth, both in the fermentor and what had been drained, by the total volume of broth produced and further dividing by the time since inoculation plus eighteen hours (to allow for turnarounds between batches). At 41.85 h after inoculation, the 1,3-propanediol titer was 108.25 g/L and broth volume in the biofermentor was 6.168 L.

Simulation of Return of Remaining Components to the Biofermentation Vessel

The effect of the invention on the operation of a biofermentor producing 1,3-propanediol was simulated by withdrawing catalyst-free broth from a biofermentor and adding to the fermentor a stream (make-up media) that approximated the composition of the stream that would being coming back to the biofermentor from the separation system.

The biofermentor, media, and inoculum were prepared as in the comparative example above.

Make-Up Media Preparation

Make up medium was prepared using the normal biofermentor medium recipe and method, except that 1) yeast extract was omitted, 2) concentration of all other non-aqueous components was reduced by 50%, and 3) 15 g/L of glycerol and 10 g/L glucose were added. Post sterilization additions to the medium, e.g., antibiotics, were also added at 50% concentration of the normal recipe.

Fermentation

Starting at 24 h after inoculation, 1 L/min of whole cell broth was withdrawn from the biofermentation vessel and passed through a cross-flow filtration unit. The cross-flow filtration unit consisted of a Pellicon-2 Mini Holder (Millipore Corporation catalog #XX42PMINI) containing a Pellicon PLC series regenerative cellulose membrane (Millipore Corporation catalog # #P2C01MV01). The membrane has a area of 0.1 $m^2$ and an nominal molecular weight limit of 1000 kilodaltons. 20 mL/min of biocatalyst-free solution was withdrawn from the cross-flow filtration unit, while cell material and the remainder of the broth were returned to the biofermentation vessel.

At the same time that the withdrawal of biocatalyst-free stream was started, 18.5 mL/min of the make-up media was fed to the biofermentor. To prevent overfilling the fermentor, 3.2 L of whole cell broth was drained from the biofermentor at 38.28 h after inoculation and 2.65 L was withdrawn at 46.81 h after inoculation.

At 52.8 h the titer in the fermentor was 75.7 g/L and the volume of broth in the biofermentor was 8.3 L. At 52.8 h after inoculation 2018 g of 1,3-propanediol had been collected in the biocatalyst-free stream withdrawn from the cross-flow filtration unit. The total volume of broth was 8.3+3.2+2.65=14.15 L. Thus, the total amount of 1,3-propanediol produced was taken to be 75.7*14.15+2018= 3089 g. The volumetric productivity at 52.8 h after inoculation was 27 kg/L/yr. Due to the decreased concentration of the inhibiting target molecule in the biofermentation vessel, the product formation rate was increased by 70%.

Example 2

Aspenplus™ Computer Simulation with Media Recycle

In this example, a steady state computer simulation was performed to predict mass flows based on known physical properties of the compounds present in the simulation.

An Aspenplus™ simulation was constructed to model a cell separation step, a water removal step and a SMB process chromatograph. A biofermentation broth feed mass composition was assumed to contain 9.606% 1,3-propanediol (the target molecule), 4.73% dry cells, 0.48% glucose, 0.961% glycerol, 0.048% acetic acid, 0.169% potassium phosphate, and the balance water. The cell separation step of the biofermentation broth removed 5% of the supernatant liquid as biocatalyst-free solution and sent the cells and the remainder of the supernatant back to the biofermentation vessel. The biocatalyst-free solution is fed to a process-to-process heat exchanger operating at about 0.196 atm. The liquid and vapor exiting the heat exchanger are separated. The liquid is the main feed to the process chromatograph. The vapor exiting the exchanger is mostly water and is compressed to about 0.2562 atm and fed to the other side of the process-to-process heat exchanger where the vapors condense. The condensate is used as the main constituent of the eluent for the SMB process chromatograph. The balance of the eluent is water separated from the product stream exiting the process chromatograph.

The process chromatograph was modeled as a 50 theoretical plate SMB with the fresh sorbent being fed to plate 1 and the eluent fed to plate 50. The liquid feed was on plate 12 and a target molecule stream was withdrawn from plate 37. The water in the target molecule-rich stream, withdrawn from plate 37, was separated from the organics and combined with the condensate from the process-to-process heat exchanger to constitute the eluent for the process chromatograph. The liquid exiting the chromatograph at plate 1 is a biocatalyst-free and target-molecule free solution. This is combined with cells and liquid from the cell separation step and is then returned to the biofermentation vessel for media recycling. Results for selected streams are in Table 3.

TABLE 2

Ratio of liquid activity coefficients in dodecane phase to activity coefficients in water phase

| | |
|---|---|
| Water | 22093 |
| 1,3-Propanediol | 0.16 |
| Glucose | 0.224 |
| Glycerol | 0.191 |
| Acetic acid | 0.784 |
| n-Dodecane | 2.07E-09 |
| Potassium Phosphate | 7.768 |

TABLE 3

| | Whole cell broth from fermentor | Vapor to compressor | Biocatalyst-free liquid to chromatograph | Eluent to chromatograph | Sorbent to chromatograph | Target rich fraction from chromatograph | Return to fermentor |
|---|---|---|---|---|---|---|---|
| Temp (° C.) | 35 | 62.8 | 62.8 | 40.17 | 50 | 40.2 | 35.98 |
| Press. (atm) | 2.0 | 0.1962 | 0.1962 | 3 | 1 | 1 | 1 |
| Composition (kg/s) | | | | | | | |
| Cell (dry wt) | 6.38 | 0 | 0 | 0 | 0 | 0 | 6.38 |
| $H_2O$ | 113.39 | 4.486 | 1.179 | 6.9871 | 0 | 2.501 | 113.3 |
| 1,3-propanediol | 12.96 | 1.26E-02 | 0.635 | 1.26E-02 | 0 | 0.4474 | 12.5 |
| Glucose | 0.6477 | 4.24E-11 | 3.24E-02 | 4.24E-11 | 0 | 2.064E-03 | 0.6457 |
| Glycerol | 1.295 | 7.38E-06 | 6.48E-02 | 7.38E-06 | 0 | 2.24E-02 | 1.273 |

TABLE 3-continued

|  | Whole cell broth from fermentor | Vapor to compressor | Biocatalyst-free liquid to chromatograph | Eluent to chromatograph | Sorbent to chromatograph | Target rich fraction from chromatograph | Return to fermentor |
|---|---|---|---|---|---|---|---|
| Acetic acid | 6.5E-02 | 2.25E-03 | 9.868E-04 | 2.25E-03 | 0 | 8.54E-04 | 6.37E-02 |
| Dodecane | 0 | 0 | 0 | 0 | 6.0 | 3.77E-08 | 1.05E-07 |

Comparative Example

Aspenplus™ Computer Simulation with No Media Recycle

In this example, a steady state computer simulation was performed as in Example 2; however there is no media recycle. The net rate at which 1,3-propanediol is removed from the biofermentation vessel in Example 2 is 0.455 kg/sec. A simulation was constructed to simulate the same net removal of 1,3-propanediol from the biofermentation vessel but with the broth components in the biocatalyst-free solution (other than the 1,3-propanediol) being replenished in the biofermentor at the same rate by adding fresh (non-recycled) media.

An Aspenplus™ simulation was constructed to model a cell separation step. A biofermentation broth feed mass composition was assumed to contain 9.606% 1,3-propanediol (the target molecule), 4.73% dry cells, 0.48% glucose, 0.961% glycerol, 0.048% acetic acid, 0.169% potassium phosphate, and the balance water. The cell separation step of the biofermentation broth removed 4.512 kg/sec of the supernatant liquid as a biocatalyst-free solution and sent the cells and the remainder of the supernatant back to the biofermentation vessel. This biocatalyst-free solution stream contains 0.455 kg/sec of 1,3-propanediol and 4.057 kg/sec of broth components other than 1,3-propanediol. It would therefore be necessary to add fresh media to the biofermentation vessel at a rate of 4.057 kg/sec (or 350,525 kg/d) to maintain the concentration of the other broth components in the biofermentation vessel.

What is claimed is:

1. A product removal process for use in a biofermentation system comprising:
   a) removing during at least a portion of the biofermentation at least a majority of biocatalyst from a portion of biofermentation solution containing a target molecule;
   b) removing a portion of water from the biocatalyst-free solution produced in step a);
   c) optionally before or after step b) removing components other than the target molecule from the biocatalyst-free solution;
   d) feeding through a chromatographic medium
      1) the biocatalyst-free solution produced by any of the steps of b) or c), and
      2) an eluent;
   e) recovering the target molecule from a first fraction of the biocatalyst-free solution discharged from the chromatographic medium;
   f) optionally removing non-aqueous eluent from a second fraction of the biocatalyst-free and target molecule-free solution discharged from the chromatographic medium;
   g) optionally adding water removed from the biocatalyst-free solution in step b) to the biocatalyst-free and target molecule-free solution after steps e) or f) in an amount suitable for return to the biofermentation; and
   h) returning the biocatalyst-free and target molecule-free solution from any of the steps of d), e), f), or g) to the biofermentation.

2. A product removal process for use in a biofermentation system, comprising:
   a) removing during at least a portion of the biofermentation at least a majority of biocatalyst from a portion of biofermentation solution containing a target molecule more volatile than water;
   b) optionally before step c) removing components other than the target molecule from the biocatalyst-free solution produced in step a);
   c) feeding through a chromatographic medium
      1) the biocatalyst-free solution of steps a) or b), and
      2) an eluent;
   d) recovering the target molecule from a first fraction of the biocatalyst-free solution discharged from the chromatographic medium;
   e) removing a portion of water from a second fraction of the biocatalyst-free and target molecule-free solution discharged from the chromatographic medium;
   f) optionally, before or after step e), removing non-aqueous eluent from the second fraction of the biocatalyst-free and target molecule-free solution discharged from the chromatographic medium; and
   g) returning the biocatalyst-free and target molecule-free solution from any of the steps of e), or f) to the biofermentation.

3. The product removal process of claim 1 or claim 2, wherein the eluent comprises water generated by the water removal step b) or step e) respectively.

4. The product removal process of claim 3, wherein the eluent comprises a mixture of water and a non-aqueous eluent.

5. The product removal process of claim 4, wherein the non-aqueous eluent is a short chain alcohol or acetone.

6. The product removal process of claim 3, wherein the eluent is water.

7. The product removal process of claim 1, wherein approximately 50–80% of water is removed from the biocatalyst-free solution of step (a).

8. The product removal process of claim 1, wherein the suitable amount of water added at step (g) returns the water concentration of the biocatalyst-free and target molecule-free solution to approximately the water concentration of the biocatalyst-free solution before step (b).

9. The product removal process of claim 1, wherein the suitable amount of water added at step g) returns the water concentration of the biocatalyst-free and target molecule-free solution to less than the water concentration of the biocatalyst-free solution before step (b).

10. The product removal process of claim 2, wherein approximately 50–80% of water is removed from the biocatalyst-free and target molecule-free solution of step (e).

11. The product removal process of claim 2, wherein the suitable amount of water added at step (g) returns the water concentration of the bio-catalyst-free and target molecule-free solution to approximately the water concentration of the biocatalyst-free solution before step (c).

12. The product removal process of claim 2, wherein the suitable amount of water added at step g) returns the water concentration of the biocatalyst-free and target molecule-free solution to less than the water concentration of the biocatalyst-free solution before step (c).

13. The process of claim 1, wherein the target molecule is 1,3-propanediol.

* * * * *

SEQUENCE LISTING

```
<160> NUMBER OF SEQ ID NOS: 1

<210> SEQ ID NO 1
<211> LENGTH: 13543
<212> TYPE: DNA
<213> ORGANISM: artificial sequence
<220> FEATURE:
<223> OTHER INFORMATION: plasmid

<400> SEQUENCE: 1
tagtaaagcc ctcgctagat tttaatgcgg atgttgcgat tacttcgcca actattgcga      60
taacaagaaa aagccagcct ttcatgatat atctcccaat ttgtgtaggg cttattatgc     120
acgcttaaaa ataataaaag cagacttgac ctgatagttt ggctgtgagc aattatgtgc     180
ttagtgcatc taacgcttga gttaagccgc gccgcgaagc ggcgtcggct tgaacgaatt     240
gttagacatt atttgccgac taccttggtg atctcgcctt tcacgtagtg gacaaattct     300
tccaactgat ctgcgcgcga ggccaagcga tcttcttctt gtccaagata agcctgtcta     360
gcttcaagta tgacgggctg atactgggcc ggcaggcgct ccattgccca gtcggcagcg     420
acatccttcg gcgcgatttt gccggttact gcgctgtacc aaatgcggga caacgtaagc     480
actacatttc gctcatcgcc agcccagtcg ggcggcgagt tccatagcgt taaggtttca     540
tttagcgcct caaatagatc ctgttcagga accggatcaa agagttcctc cgccgctgga     600
cctaccaagg caacgctatg ttctcttgct tttgtcagca agatagccag atcaatgtcg     660
atcgtggctg gctcgaagat acctgcaaga atgtcattgc gctgccattc tccaaattgc     720
agttcgcgct tagctggata acgccacgga atgatgtcgt cgtgcacaac aatggtgact     780
tctacagcgc ggagaatctc gctctctcca ggggaagccg aagtttccaa aaggtcgttg     840
atcaaagctc gccgcgttgt ttcatcaagc cttacggtca ccgtaaccag caaatcaata     900
tcactgtgtg gcttcaggcc gccatccact gcggagccgt acaaatgtac ggccagcaac     960
```

-continued

```
gtcggttcga gatggcgctc gatgacgcca actacctctg atagttgagt cgatacttcg    1020
gcgatcaccg cttccctcat gatgtttaac tttgttttag ggcgactgcc ctgctgcgta    1080
acatcgttgc tgctccataa catcaaacat cgacccacgg cgtaacgcgc ttgctgcttg    1140
gatgcccgag gcatagactg taccccaaaa aaacagtcat aacaagccat gaaaaccgcc    1200
actgcgccgt taccaccgct gcgttcggtc aaggttctgg accagttgcg tgagcgcata    1260
cgctacttgc attacagctt acgaaccgaa caggcttatg tccactgggt tcgtgccttc    1320
atccgtttcc acggtgtgcg tcacccggca accttgggca gcagcgaagt cgaggcattt    1380
ctgtcctggc tggcgaacga gcgcaaggtt tcggtctcca cgcatcgtca ggcattggcg    1440
gccttgctgt tcttctacgg caaggtgctg tgcacggatc tgccctggct tcaggagatc    1500
ggaagacctc ggccgtcgcg gcgcttgccg gtggtgctga ccccggatga agtggttcgc    1560
atcctcggtt ttctggaagg cgagcatcgt tgttcgccc agcttctgta tggaacgggc    1620
atgcggatca gtgagggttt gcaactgcgg gtcaaggatc tggatttcga tcacggcacg    1680
atcatcgtgc gggagggcaa gggctccaag gatcgggcct tgatgttacc cgagagcttg    1740
gcacccagcc tgcgcgagca ggggaattaa ttcccacggg ttttgctgcc cgcaaacggg    1800
ctgttctggt gttgctagtt tgttatcaga atcgcagatc cggcttcagc cggtttgccg    1860
gctgaaagcg ctattcttc cagaattgcc atgattttt ccccacggga ggcgtcactg    1920
gctcccgtgt tgtcggcagc tttgattcga taagcagcat cgcctgtttc aggctgtcta    1980
tgtgtgactg ttgagctgta acaagttgtc tcaggtgttc aatttcatgt tctagttgct    2040
ttgttttact ggtttcacct gttctattag gtgttacatg ctgttcatct gttacattgt    2100
cgatctgttc atggtgaaca gctttgaatg caccaaaaac tcgtaaaagc tctgatgtat    2160
ctatcttttt tacaccgttt tcatctgtgc atatggacag ttttcccttt gatatgtaac    2220
ggtgaacagt tgttctactt tgtttgtta gtcttgatgc ttcactgata gatacaagag    2280
ccataagaac ctcagatcct tccgtattta gccagtatgt tctctagtgt ggttcgttgt    2340
ttttgcgtga gccatgagaa cgaaccattg agatcatact tactttgcat gtcactcaaa    2400
aattttgcct caaaactggt gagctgaatt tttgcagtta aagcatcgtg tagtgttttt    2460
cttagtccgt tatgtaggta ggaatctgat gtaatggttg ttggtatttt gtcaccattc    2520 attttatct ggttgttctc aagttcggtt acgagatcca tttgtctatc tagttcaact    2580
tggaaaatca acgtatcagt cgggcggcct cgcttatcaa ccaccaattt catattgctg    2640
taagtgttta aatctttact tattggtttc aaaacccatt ggttaagcct tttaaactca    2700
tggtagttat tttcaagcat taacatgaac ttaaattcat caaggctaat ctctatattt    2760
gccttgtgag ttttcttttg tgttagttct tttaataacc actcataaat cctcatagag    2820
tatttgtttt caaagacttt aacatgttcc agattatatt ttatgaattt ttttaactgg    2880
aaaagataag gcaatatctc ttcactaaaa actaattcta atttttcgct tgagaacttg    2940
gcatagtttg tccactggaa aatctcaaag cctttaacca aaggattcct gatttccaca    3000
gttctcgtca tcagctctct ggttgcttta gctaatacac cataagcatt ttccctactg    3060
atgttcatca tctgagcgta ttggttataa gtgaacgata ccgtccgttc tttccttgta    3120
gggttttcaa tcgtggggtt gagtagtgcc acacagcata aaattagctt ggtttcatgc    3180
tccgttaagt catagcgact aatcgctagt tcatttgctt tgaaaacaac taattcagac    3240
atacatctca attggtctag gtgattttaa tcactatacc aattgagatg ggctagtcaa    3300
tgataattac tagtcctttt cctttgagtt gtgggtatct gtaaattctg ctagacctttt    3360
```

-continued

```
gctggaaaac ttgtaaattc tgctagaccc tctgtaaatt ccgctagacc tttgtgtgtt   3420 tttttttgttt atattcaagt ggttataatt tatagaataa agaaagaata aaaaaagata   3480
aaaagaatag atcccagccc tgtgtataac tcactacttt agtcagttcc gcagtattac   3540
aaaaggatgt cgcaaacgct gtttgctcct ctacaaaaca gaccttaaaa ccctaaaggc   3600
ttaagtagca ccctcgcaag ctcgggcaaa tcgctgaata ttccttttgt ctccgaccat   3660
caggcacctg agtcgctgtc ttttttcgtga cattcagttc gctgcgctca cggctctggc   3720
agtgaatggg ggtaaatggc actacaggcg ccttttatgg attcatgcaa ggaaactacc   3780
cataatacaa gaaaagcccg tcacgggctt ctcagggcgt tttatggcgg gtctgctatg   3840
tggtgctatc tgacttttg ctgttcagca gttcctgccc tctgattttc cagtctgacc   3900
acttcggatt atcccgtgac aggtcattca gactggctaa tgcacccagt aaggcagcgg   3960
tatcatcaac aggcttaccc gtcttactgt cgggaattca tttaaatagt caaaagcctc   4020
cgaccggagg cttttgactg ctaggcgatc tgtgctgttt ccacggtat gcagcaccag   4080 cgcgagatta tgggctcgca cgctcgactg tcggacgggg gcactggaac gagaagtcag   4140
gcgagccgtc acgcccttga ctatgccaca tcctgagcaa ataattcaac cactaaacaa   4200
atcaaccgcg tttccccggag gtaaccaagc ttgcgggaga gaatgatgaa caagagccaa   4260
caagttcaga caatcaccct ggccgccgcc cagcaaatgg cggcggcggt ggaaaaaaaa   4320
gccactgaga tcaacgtggc ggtggtgttt tccgtagttg accgcggagg caacacgctg   4380
cttatccagc ggatggacga ggccttcgtc tccagctgcg atatttccct gaataaagcc   4440
tggagcgcct gcagcctgaa gcaaggtacc catgaaatta cgtcagcggt ccagccagga   4500
caatctctgt acggtctgca gctaaccaac caacagcgaa ttattatttt tggcggcggc   4560
ctgccagtta ttttttaatga gcaggtaatt ggcgccgtcg gcgttagcgg cggtacggtc   4620
gagcaggatc aattattagc ccagtgcgcc ctggattgtt tttccgcatt ataacctgaa   4680
gcgagaaggt atattatgag ctatcgtatg ttccgccagg cattctgagt gttaacgagg   4740
ggaccgtcat gtcgctttca ccgccaggcg tacgcctgtt ttacgatccg cgcgggcacc   4800
atgccggcgc catcaatgag ctgtgctggg ggctggagga gcaggggtc ccctgccaga   4860 ccataaccta tgacggaggc ggtgacgccg ctgcgctggg cgccctggcg ccagaagct   4920 cgcccctgcg ggtgggtatc gggctcagcg cgtccggcga gatagccctc actcatgccc   4980
agctgccggc ggacgcgccg ctggctaccg gacacgtcac cgatagcgac gatcaactgc   5040
gtacgctcgg cgccaacgcc gggcagctgg ttaaagtcct gccgttaagt gagagaaact   5100
gaatgtatcg tatctatacc cgcaccgggg ataaaggcac caccgccctg tacggcggca   5160
gccgcatcga gaaagaccat attcgcgtcg aggcctacgg caccgtcgat gaactgatat   5220
cccagctggg cgtctgctac gccacgaccc gcgacgccgg gctgcgggaa agcctgcacc   5280
atattcagca gacgctgttc gtgctggggg ctgaactggc cagcgatgcg cggggcctga   5340
cccgcctgag ccagacgatc ggcgaagagg agatcaccgc cctggagcgg cttatcgacc   5400
gcaatatggc cgagagcggc ccgttaaaac agttcgtgat cccgggggagg aatctcgcct   5460 ctgcccagct gcacgtggcg cgcacccagt cccgtcggct cgaacgcctg ctgacggcca   5520
tggaccgcgc gcatccgctg cgcgacgcgc tcaaacgcta cagcaatcgc ctgtcggatg   5580
ccctgttctc catggcgcga atcgaagaga ctaggcctga tgcttgcgct tgaactggcc   5640
tagcaaacac agaaaaaagc ccgcacctga cagtgcgggc ttttttttc ctaggcgatc   5700 tgtgctgttt ccacggtat gcagcaccag cgcgagatta tgggctcgca cgctcgactg   5760
```

-continued

```
tcggacgggg gcactggaac gagaagtcag gcgagccgtc acgcccttga ctatgccaca      5820
tcctgagcaa ataattcaac cactaaacaa atcaaccgcg tttcccggag gtaaccaagc      5880
ttcacctttt gagccgatga acaatgaaaa gatcaaaacg atttgcagta ctggcccagc      5940
gccccgtcaa tcaggacggg ctgattggcg agtggcctga agaggggctg atcgccatgg      6000
acagcccctt tgacccggtc tcttcagtaa aagtggacaa cggtctgatc gtcgaactgg      6060
acggcaaacg ccgggaccag tttgacatga tcgaccgatt tatcgccgat tacgcgatca      6120
acgttgagcg cacagagcag gcaatgcgcc tggaggcggt ggaaatagcc cgtatgctgg      6180
tggatattca cgtcagccgg gaggagatca ttgccatcac taccgccatc acgccggcca      6240
aagcggtcga ggtgatggcg cagatgaacg tggtggagat gatgatggcg ctgcagaaga      6300
tgcgtgcccg ccggaccccc tccaaccagt gccacgtcac caatctcaaa gataatccgg      6360
tgcagattgc cgctgacgcc gccgaggccg ggatccgcgg cttctcagaa caggagacca      6420
cggtcggtat cgcgcgctac gcgccgttta acgccctggc gctgttggtc ggttcgcagt      6480
gcggccgccc cggcgtgttg acgcagtgct cggtggaaga ggccaccgag ctggagctgg      6540
gcatgcgtgt cttaaccagc tacgccgaga cggtgtcggt ctacggcacc gaagcggtat      6600
ttaccgacgg cgatgatacg ccgtggtcaa aggcgttcct cgcctcggcc tacgcctccc      6660
gcgggttgaa aatgcgctac acctccggca ccggatccga agcgctgatg ggctattcgg      6720
agagcaagtc gatgctctac ctcgaatcgc gctgcatctt cattactaaa ggcgccgggg      6780
ttcagggact gcaaaacggc gcggtgagct gtatcggcat gaccggcgct gtgccgtcgg      6840
gcattcgggc ggtgctggcg gaaaacctga tcgcctctat gctcgacctc gaagtggcgt      6900
ccgccaacga ccagactttc tcccactcgg atattgccg caccgcgcgc accctgatgc      6960
agatgctgcc gggcaccgac tttatttttct ccggctacag cgcggtgccg aactacgaca      7020
acatgttcgc cggctcgaac ttcgatgcgg aagattttga tgattacaac atcctgcagc      7080
gtgacctgat ggttgacggc ggcctgcgtc cggtgaccga ggcggaaacc attgccattc      7140
gccagaaagc ggcgcgggcg atccaggcgg ttttccgcga gctggggctg ccgccaatcg      7200
ccgacgagga ggtggaggcc gccacctacg cgcacggcag caacgagatg ccgccgcgta      7260
acgtggtgga ggatctgagt gcggtggaag agatgatgaa cgcaacatc accggcctcg      7320 atattgtcgg cgcgctgagc cgcagcggct ttgaggatat cgccagcaat attctcaata      7380
tgctgcgcca gcgggtcacc ggcgattacc tgcagacctc ggccattctc gatcggcagt      7440
tcgaggtggt gagtgcggtc aacgacatca atgactatca ggggccgggc accggctatc      7500
gcatctctgc cgaacgctgg gcggagatca aaaatattcc gggcgtggtt cagcccgaca      7560
ccattgaata aggcggtatt cctgtgcaac agacaaccca aattcagccc tcttttaccc      7620
tgaaaacccg cgagggcggg gtagcttctg ccgatgaacg cgccgatgaa gtggtgatcg      7680
gcgtcggccc tgccttcgat aaacaccagc atcacactct gatcgatatg ccccatggcg      7740
cgatcctcaa agagctgatt gccggggtgg aagaagaggg gcttcacgcc cggtggtgc      7800 gcattctgcg cacgtccgac gtctccttta tggcctggga tgcggccaac ctgagcggct      7860
cggggatcgg catcggtatc cagtcgaagg ggaccacggt catccatcag cgcgatctgc      7920
tgccgctcag caacctggag ctgttctccc aggcgccgct gctgacgctg agacctacc      7980 ggcagattgg caaaaacgct gcgcgctatg cgcgcaaaga gtcaccttcg ccggtgccgg      8040
tggtgaacga tcagatggtg cggccgaaat ttatggccaa agccgcgcta tttcatatca      8100
aagagaccaa acatgtggtg caggacgccg agcccgtcac cctgcacatc gacttagtaa      8160
```

-continued

```
gggagtgacc atgagcgaga aaaccatgcg cgtgcaggat tatccgttag ccacccgctg   8220
cccggagcat atcctgacgc ctaccggcaa accattgacc gatattaccc tcgagaaggt   8280
gctctctggc gaggtgggcc cgcaggatgt gcggatctcc cgccagaccc ttgagtacca   8340
ggcgcagatt gccgagcaga tgcagcgcca tgcggtggcg cgcaatttcc gccgcgcggc   8400
ggagcttatc gccattcctg acgagcgcat tctggctatc tataacgcgc tgcgcccgtt   8460
ccgctcctcg caggcggagc tgctggcgat cgccgacgag ctggagcaca cctggcatgc   8520
gacagtgaat gccgcttttg tccgggagtc ggcggaagtg tatcagcagc ggcataagct   8580
gcgtaaagga agctaagcgg aggtcagcat gccgttaata ccgggattg atatcggcaa   8640 cgccaccacc gaggtggcgc tggcgtccga ctacccgcag gcgagggcgt ttgttgccag   8700
cgggatcgtc gcgacgacgg gcatgaaagg gacgcgggac aatatcgccg ggaccctcgc   8760
cgcgctggag caggccctgg cgaaaacacc gtggtcgatg agcgatgtct ctcgcatcta   8820
tcttaacgaa gccgcgccgg tgattggcga tgtggcgatg gagaccatca ccgagaccat   8880
tatcaccgaa tcgaccatga tcggtcataa cccgcagacg ccgggcgggg tgggcgttgg   8940
cgtggggacg actatcgccc tcgggcggct ggcgacgctg ccggcggcgc agtatgccga   9000
ggggtggatc gtactgattg acgacgccgt cgatttcctt gacgccgtgt ggtggctcaa   9060
tgaggcgctc gaccggggga tcaacgtggt ggcggcgatc ctcaaaaagg acgacgcgt   9120 gctggtgaac aaccgcctgc gtaaaaccct gccggtggtg gatgaagtga cgctgctgga   9180
gcaggtcccc gaggggtaa tggcggcggt ggaagtggcc gcgccgggcc aggtggtgcg   9240
gatcctgtcg aatccctacg ggatcgccac cttcttcggg ctaagcccgg aagagaccca   9300
ggccatcgtc cccatcgccc gcgccctgat tggcaaccgt tccgcggtgg tgctcaagac   9360
cccgcagggg gatgtgcagt cgcgggtgat cccggcgggc aacctctaca ttagcggcga   9420
aaagcgccgc ggagaggccg atgtcgccga gggcgcggaa gccatcatgc aggcgatgag   9480
cgcctgcgct ccggtacgcg acatccgcgg cgaaccgggc acccacgccg gcggcatgct   9540
tgagcgggtg cgcaaggtaa tggcgtccct gaccggccat gagatgagcg cgatatacat   9600
ccaggatctg ctggcggtgg atacgtttat tccgcgcaag gtgcagggcg ggatggccgg   9660
cgagtgcgcc atggagaatg ccgtcgggat ggcggcgatg gtgaaagcgg atcgtctgca   9720
aatgcaggtt atcgcccgcg aactgagcgc ccgactgcag accgaggtgg tggtgggcgg   9780
cgtggaggcc aacatggcca tcgccggggc gttaaccact cccggctgtg cggcgccgct   9840
ggcgatcctc gacctcggcg ccggctcgac ggatgcggcg atcgtcaacg cggagggggca   9900 gataacggcg gtccatctcg ccggggcggg gaatatggtc agcctgttga ttaaaaccga   9960
gctgggcctc gaggatcttt cgctggcgga agcgataaaa aaatacccgc tggccaaagt  10020
ggaaagcctg ttcagtattc gtcacgagaa tggcgcggtg gagttctttc gggaagccct  10080
cagcccggcg gtgttcgcca agtggtgta catcaaggag ggcgaactgg tgccgatcga  10140
taacgccagc ccgctggaaa aaattcgtct cgtgcgccgg caggcgaaag agaaagtgtt  10200
tgtcaccaac tgcctgcgcg cgctgcgcca ggtctcaccc ggcggttcca ttcgcgatat  10260
cgcctttgtg gtgctggtgg gcggctcatc gctggacttt gagatcccgc agcttatcac  10320
ggaagccttg tcgcactatg gcgtggtcgc cgggcagggc aatattcggg gaacagaagg  10380
gccgcgcaat gcggtcgcca ccgggctgct actggccggt caggcgaatt aaacgggcgc  10440
tcgcgccagc ctctaggtac aaataaaaaa ggcacgtcag atgacgtgcc ttttttcttg  10500
tctagcgtgc accaatgctt ctggcgtcag gcagccatcg gaagctgtgg tatggctgtg  10560
```

-continued

```
caggtcgtaa atcactgcat aattcgtgtc gctcaaggcg cactcccgtt ctggataatg    10620 tttttttgcgc cgacatcata acggttctgg caaatattct gaaatgagct gttgacaatt  10680
aatcatccgg ctcgtataat gtgtggaatt gtgagcggat aacaatttca cacaggaaac   10740
agaccatgac tagtaaggag gacaattcca tggctgctgc tgctgataga ttaaacttaa   10800
cttccggcca cttgaatgct ggtagaaaga gaagttcctc ttctgtttct ttgaaggctg   10860
ccgaaaagcc tttcaaggtt actgtgattg gatctggtaa ctggggtact actattgcca   10920
aggtggttgc cgaaaattgt aagggatacc cagaagtttt cgctccaata gtacaaatgt   10980
gggtgttcga agaagagatc aatggtgaaa aattgactga aatcataaat actagacatc   11040
aaaacgtgaa atacttgcct ggcatcactc tacccgacaa tttggttgct aatccagact   11100
tgattgattc agtcaaggat gtcgacatca tcgttttcaa cattccacat caattttgc    11160 cccgtatctg tagccaattg aaaggtcatg ttgattcaca cgtcagagct atctcctgtc   11220
taaagggttt tgaagttggt gctaaaggtg tccaattgct atcctcttac atcactgagg   11280
aactaggtat tcaatgtggt gctctatctg gtgctaacat tgccaccgaa gtcgctcaag   11340
aacactggtc tgaaacaaca gttgcttacc acattccaaa ggatttcaga ggcgagggca   11400
aggacgtcga ccataaggtt ctaaaggcct tgttccacag accttacttc cacgttagtg   11460
tcatcgaaga tgttgctggt atctccatct gtggtgcttt gaagaacgtt gttgccttag   11520
gttgtggttt cgtcgaaggt ctaggctggg gtaacaacgc ttctgctgcc atccaaagag   11580
tcggtttggg tgagatcatc agattcggtc aaatgttttt cccagaatct agagaagaaa   11640
catactacca agagtctgct ggtgttgctg atttgatcac cacctgcgct ggtggtagaa   11700
acgtcaaggt tgctaggcta atggctactt ctggtaagga cgcctgggaa tgtgaaaagg   11760
agttgttgaa tggccaatcc gctcaaggtt taattacctg caaagaagtt cacgaatggt   11820
tggaaacatg tggctctgtc gaagacttcc cattatttga agccgtatac caaatcgttt   11880
acaacaacta cccaatgaag aacctgccgg acatgattga agaattagat ctacatgaag   11940
attagattta ttggatccag gaaacagact agaattatgg gattgactac taaacctcta   12000
tctttgaaag ttaacgccgc tttgttcgac gtcgacggta ccattatcat ctctcaacca   12060
gccattgctg cattctggag ggatttcggt aaggacaaac cttatttcga tgctgaacac   12120
gttatccaag tctcgcatgg ttggagaacg tttgatgcca ttgctaagtt cgctccagac   12180
tttgccaatg aagagtatgt taacaaatta gaagctgaaa ttccggtcaa gtacggtgaa   12240
aaatccattg aagtcccagg tgcagttaag ctgtgcaacg ctttgaacgc tctaccaaaa   12300
gagaaatggg ctgtggcaac ttccggtacc cgtgatatgg cacaaaaatg gttcgagcat  12360
ctgggaatca ggagaccaaa gtacttcatt accgctaatg atgtcaaaca gggtaagcct   12420
catccagaac catatctgaa gggcaggaat ggcttaggat atccgatcaa tgagcaagac   12480
ccttccaaat ctaaggtagt agtatttgaa gacgctccag caggtattgc cgccggaaaa   12540
gccgccggtt gtaagatcat tggtattgcc actactttcg acttggactt cctaaaggaa   12600
aaaggctgtg acatcattgt caaaaaccac gaatccatca gagttggcgg ctacaatgcc   12660
gaaacagacg aagttgaatt cattttttgac gactacttat atgctaagga cgatctgttg   12720
aaatggtaac ccgggctgca ggcatgcaag cttggctgtt ttggcggatg agaagagatt   12780
ttcagcctga tacagattaa atcagaacgc agaagcggtc tgataaaaca gaatttgcct   12840
ggcggcagta gcgcggtggt cccacctgac cccatgccga actcagaagt gaaacgccgt   12900
agcgccgatg gtagtgtggg gtctccccat gcgagagtag ggaactgcca ggcatcaaat   12960
```

```
                                              -continued aaaacgaaag gctcagtcga aagactgggc ctttcgtttt atctgttgtt tgtcggtgaa   13020
cgctctcctg agtaggacaa atccgccggg agcggatttg aacgttgcga agcaacggcc   13080
cggagggtgg cgggcaggac gcccgccata aactgccagg catcaaatta agcagaaggc   13140
catcctgacg gatggccttt ttgcgtttct acaaactcca gctggatcgg gcgctagagt   13200
atacatttaa atggtaccct ctagtcaagg ccttaagtga gtcgtattac ggactggccg   13260
tcgttttaca acgtcgtgac tgggaaaacc ctggcgttac ccaacttaat cgccttgcag   13320
cacatccccc tttcgccagc tggcgtaata gcgaagaggc ccgcaccgat cgccttccc    13380 aacagttgcg cagcctgaat ggcgaatggc gcctgatgcg gtattttctc cttacgcatc   13440
tgtgcggtat ttcacaccgc atatggtgca ctctcagtac aatctgctct gatgccgcat   13500
agttaagcca gccccgacac ccgccaacac ccgctgacga gct                    13543
```